US00PP27313P2

(12) United States Plant Patent
de Jong

(10) Patent No.: US PP27,313 P2
(45) Date of Patent: Oct. 25, 2016

(54) *ARGYRANTHEMUM* PLANT NAMED 'CHQZ0006'

(50) Latin Name: *Argyranthemum frutescens*
Varietal Denomination: CHQZ0006

(71) Applicant: SYNGENTA PARTICIPATIONS AG, Basel (CH)

(72) Inventor: Erwin de Jong, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 71 days.

(21) Appl. No.: 14/544,772

(22) Filed: Feb. 13, 2015

(51) Int. Cl.
*A01H 5/02* (2006.01)

(52) U.S. Cl.
USPC ..... Plt./406

(58) Field of Classification Search
USPC ..... Plt./263.1, 406
See application file for complete search history.

*Primary Examiner* — Susan McCormick Ewoldt
*Assistant Examiner* — Karen Redden
(74) *Attorney, Agent, or Firm* — Joshua L. Price

(57) ABSTRACT

A new *Argyranthemum* plant named 'CHQZ0006' particularly distinguished by the large, white flowers, dark-green to grey-green foliage, upright and mounding plant habit with good branching.

1 Drawing Sheet

Latin name of the genus and species of the plant claimed: *Argyranthemum frutescens.*

Varietal denomination: 'CHQZ0006'.

BACKGROUND OF THE NEW PLANT

The present invention comprises a new *Argyranthemum*, botanically known as *Argyranthemum frutescens*, and hereinafter referred to by the variety name 'CHQZ0006'.

'CHQZ0006' is a product of a planned breeding program. The new cultivar has large, white flowers, dark-green to grey-green foliage, upright and mounding plant habit with good branching.

'CHQZ0006' originated from an open pollination in the summer of 2007 in an outdoor breeding environment in Andijk, Netherlands.

The female parent was the unpatented plant named 'Sas Whit09' and commercially known as Sassy White '09', with white flowers and a taller plant than 'CHQZ0006'. The male parent is unknown because of the open pollination.

The seed was collected and sown in mid-September 2007.

'CHQZ0006' was selected as one flowering plant within the progeny in January 2008 in a greenhouse in Andijk, Netherlands.

The first act of asexual reproduction of 'CHQZ0006' was accomplished when vegetative cuttings were propagated from the initial selection in January 2008 in a controlled environment in Andijk, Netherlands.

BRIEF SUMMARY OF INVENTION

Horticultural examination of plants grown from cuttings of the plant initiated in April 2008, and continuing thereafter, has demonstrated that the combination of characteristics as herein disclosed for 'CHQZ0006' are firmly fixed and are retained through successive generations of asexual reproduction.

'CHQZ0006' has not been observed under all possible environmental conditions. The phenotype may vary significantly with variations in environment such as temperature and light intensity.

A Plant Breeder's Right for this cultivar was applied for in the European Union on Jun. 27, 2014; No. 2014/1715. 'CHQZ0006' has not been made publicly available more than one year prior to the filing of this application.

The following traits have been repeatedly observed and are determined to be basic characteristics of the new variety. The combination of these characteristics distinguishes this *Argyranthemum* as a new and distinct variety.

BRIEF DESCRIPTION OF THE PHOTOGRAPHS

The accompanying photographic drawings show typical plant and flower characteristics of 'CHQZ0006' with colors being as true as possible with an illustration of this type.

Figure 1:
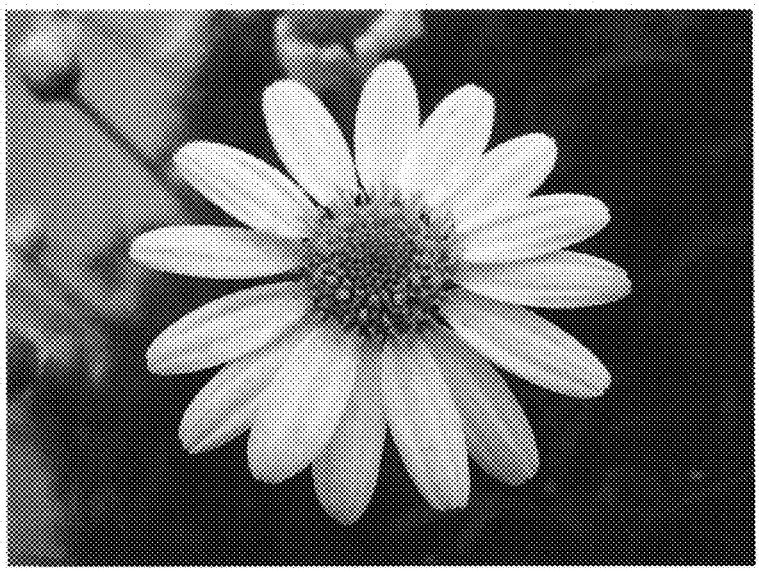
Figure 2:
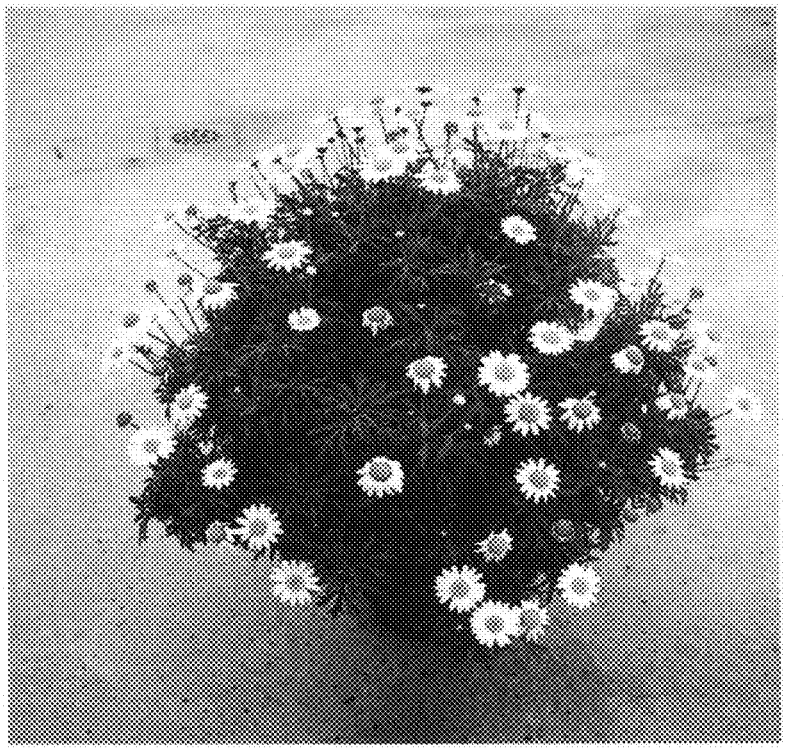

FIG. 1 shows a close-up of a flower, and FIG. 2 shows a whole flowering plant.

DETAILED BOTANICAL DESCRIPTION

The aforementioned photographs were taken in January 2015 from plants growing in a greenhouse in Enkhuizen Netherlands. These plants were growing in 19 cm pots and were approximately 18 week old from planting (potting) date.

The plant descriptions and measurements were taken in early January 2015 in Enkhuizen, Netherlands, on the same 18 week old plants. Rooted cuttings had been planted and were grown in the greenhouse at a minimum temperature of 16-18° C. day and night, from late July 2014 on.

Color references are made to The Royal Horticultural Society Colour Chart (R.H.S.) 2001.

TABLE 1

DIFFERENCES BETWEEN THE NEW VARIETY 'CHQZ0006' AND A SIMILAR VARIETY (based on measurements January 2015)

| Trait | 'CHQZ0006' | 'Argymonwhi', commercially 'Sassy (L) White', U.S. Pat. No. PP17,136 |
|---|---|---|
| Earliness, start of flowering: | Slightly later | Slightly earlier |
| Floriferousness: | More flowers | Fewer flowers |
| Flower diameter: | 3.2-3.7 cm | 3.0-3.5 cm |
| Quantity of ray florets: | 14-19 | 12-18 |
| Foliage color: | Dark(er) green RHS 131B-131C or 132B | Medium green, RHS 141B to 141C |
| Peduncle length: | 5-8 cm | 8-10 cm |
| Plant size: | 50 cm diameter 35 cm in height | 60 cm diameter, 30 cm in height |
| Tolerance to higher pH values: | Good | Poor |

Plant:

*Form, growth and habit.*—Upright and mounding, well branched, strong vigor.

*Plant height.*—30.0 cm.

*Plant height (inflorescence included).*—35.0 cm.

*Plant width.*—50.0 cm.

Roots:

*Number of days to initiate and produce roots.*—20-28 days at about 19 degrees C.

*Type.*—Fine, fibrous, free branching.

*Color.*—RHS N155B.

Foliage:

*Arrangement.*—Alternate.

*Immature, leaf color, upper surface.*—Closest to RHS N134A.

*Lower surface.*—Closest to RHS N134C.

*Mature, leaf color, upper surface.*—RHS 131B-C/RHS 132A-B.

*Lower surface.*—Closest to RHS N134C.

*Length.*—2.8-4.2 cm.

*Width.*—3.2 cm at the maximum.

*Shape.*—Pinnate.

*Base shape.*—Attenuate.

*Apex shape.*—Acute.

*Margin.*—Pinnatisect.

*Texture, upper surface.*—Smooth, glabrous.

*Lower surface.*—Closest to RHS N134C.

*Color of veins, upper surface.*—Closest to RHS 132A-B.

*Color of veins, lower surface.*—Closest to RHS N134C.

Stem:

*Quantity of main branches per plant.*—About 10-12.

*Color of stem.*—Closest to RHS 135D.

*Length of stem.*—About 7-10 cm.

*Diameter.*—0.2-0.3 cm.

*Length of internodes.*—0.5-0.9 cm.

*Texture.*—Glabrous, though slightly grooved.

*Color of peduncle.*—RHS 143A to RHS 135C.

*Length of peduncle.*—About 5.0-8.0 cm in wintertime.

*Peduncle diameter.*—0.15-0.2 cm.

*Texture.*—Glabrous, though slightly grooved.

Inflorescence:

*Type.*—Daisy-type inflorescences; disc and ray florets develop acropetally on a capitulum. Inflorescences held upright and outwardly on terminal peduncles.

*Quantity of inflorescences per plant.*—70-80.

*Lastingness of individual blooms on the plant.*—About 10 days.

*Fragrance.*—None.

Bud (just before opening/showing color):

*Color.*—RHS 4D.

*Length.*—0.7 cm.

*Width.*—0.6-0.8 cm.

*Shape.*—Initially round to ovate, turning cylindrical and cup-shaped with development of the rays.

Immature inflorescence:

*Diameter.*—2.0-2.5 cm.

*Color of ray florets, upper surface.*—Closest to RHS N155B.

*Lower surface.*—Closest to RHS N155B.

Mature inflorescence:

*Diameter.*—3.2-3.7 cm.

*Depth.*—About 0.7 cm.

*Total diameter of 'disc'.*—1.2 cm.

*Receptacle height.*—Approximately 0.4 cm.

*Receptacle diameter.*—1.1-1.3 cm.

Ray florets:

*Average quantity of florets.*—14-19 in 1 to 2 whorls.

*Color of florets, upper surface.*—Whiter than RHS 155D.

*Lower surface.*—Whiter than RHS 155D.

*Length.*—Approximately 1.2 cm.

*Width.*—0.5-0.6 cm.

*Shape.*—Ligulate.

*Apex shape.*—Mucronulate.

*Margin.*—Entire.

*Texture, upper surface.*—Glabrous, smooth, grooved lengthwise.

*Lower surface.*—Glabrous to rugose, with 2 protruding veins.

Disc florets:

*Average quantity of florets.*—About 60-80.

*Color of florets.*—RHS 145A (closed floret) to RHS 1A-B at open floret.

*Length.*—0.2 cm.

*Width.*—0.05 cm.

*Shape.*—Tubular, elongated.

*Apex shape.*—Acute, 5 pointed.

Phyllaries:

*Quantity.*—15 or more.

*Color, upper surface.*—RHS N144A with transparent margins.

*Lower surface.*—RHS N144B with transparent margins.

*Length.*—0.2-0.3 cm.

*Width.*—0.2 cm.

*Shape.*—Ovate to obovate.

*Apex shape.*—Elliptic.

*Base.*—Fused.

*Margins.*—Entire.

*Texture, upper surface.*—Glabrous with papery margins.

*Lower surface.*—Glabrous with papery margins.

REPRODUCTIVE ORGANS

Gynoecium:

*Pistil.*—1, found on both florets.

*Length.*—0.4-0.5 cm.

*Style color*.—RHS 145D.
*Style length*.—0.3 cm.
*Stigma color*.—RHS 13A.
*Stigma shape*.—Bi-furcate.

Androecium:

*Stamens*.—1, found on only disc florets.
*Color of filaments*.—RHS 2B.
*Length filaments*.—0.15-0.2 cm.
*Anther color*.—RHS 13A.
*Anther length*.—0.15-0.2 cm.
*Anther shape*.—Oval to club shaped.
*Color of pollen*.—RHS 13A.
*Pollen amount*.—Moderate.

Fertility/seed set: Fertility/seed set has not been observed on this hybrid.

Disease/pest resistance: Disease/pest resistance has not been observed on this hybrid.

What is claimed is:

1. A new and distinct variety of *Argyranthemum* plant named 'CHQZ0006' substantially as illustrated and described herein.

* * * * *